United States Patent [19]

Van Eck

[11] 4,130,117

[45] Dec. 19, 1978

[54] HYPODERMIC SYRINGE

[76] Inventor: William F. Van Eck, 228 Main St., East Haven, Conn. 06512

[21] Appl. No.: 723,192

[22] Filed: Sep. 15, 1976

Related U.S. Application Data

[60] Division of Ser. No. 501,448, Aug. 28, 1974, Pat. No. 3,989,045, which is a continuation of Ser. No. 293,489, Sep. 29, 1972, abandoned.

[51] Int. Cl.² ............................................... A61M 5/00
[52] U.S. Cl. ..................................... 128/216; 128/272
[58] Field of Search ....................... 128/216, 272, 232; 222/541

[56] References Cited

U.S. PATENT DOCUMENTS

| | | | |
|---|---|---|---|
| 2,397,051 | 3/1946 | Scherer | 128/272 |
| 2,552,870 | 5/1951 | Scherer | 128/272 |
| 2,895,475 | 7/1959 | Cole | 128/272 |
| 3,736,933 | 6/1973 | Szabo | 128/216 |

Primary Examiner—William E. Kamm
Assistant Examiner—Henry S. Layton
Attorney, Agent, or Firm—DeLio and Montgomery

[57] ABSTRACT

A hypodermic syringe including a needle and a deformable ampul connected thereto adjacent a neck portion where a rupturable membrane extends across the neck portion sealing a medicament in the ampul.

9 Claims, 23 Drawing Figures

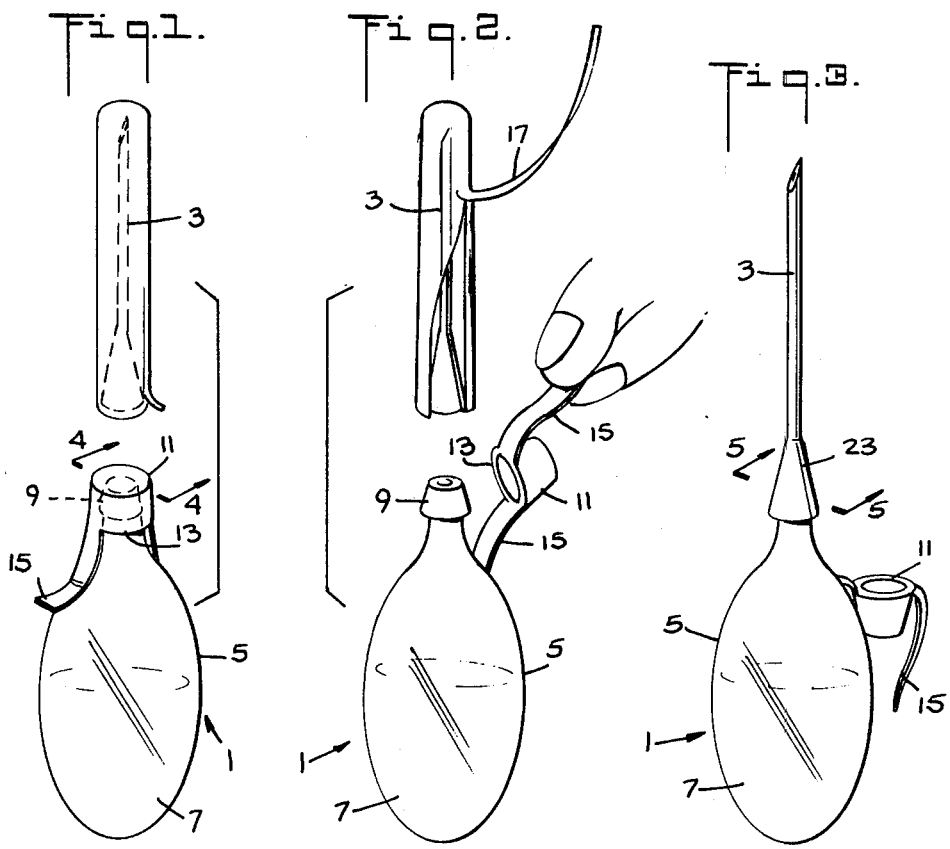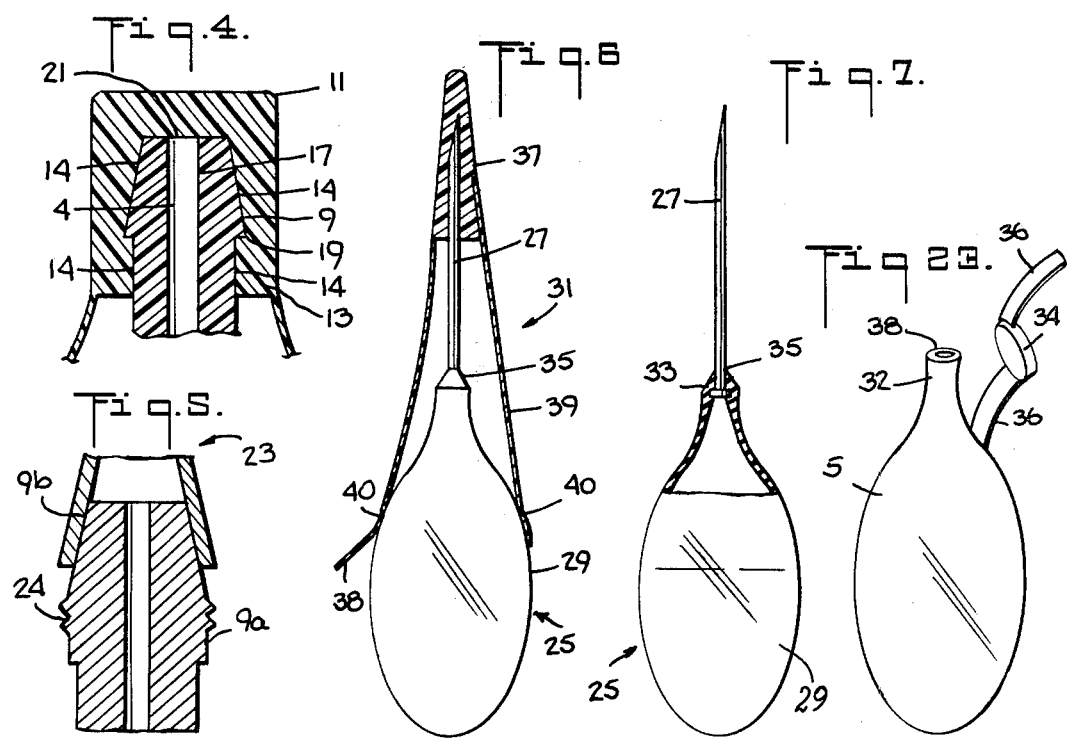

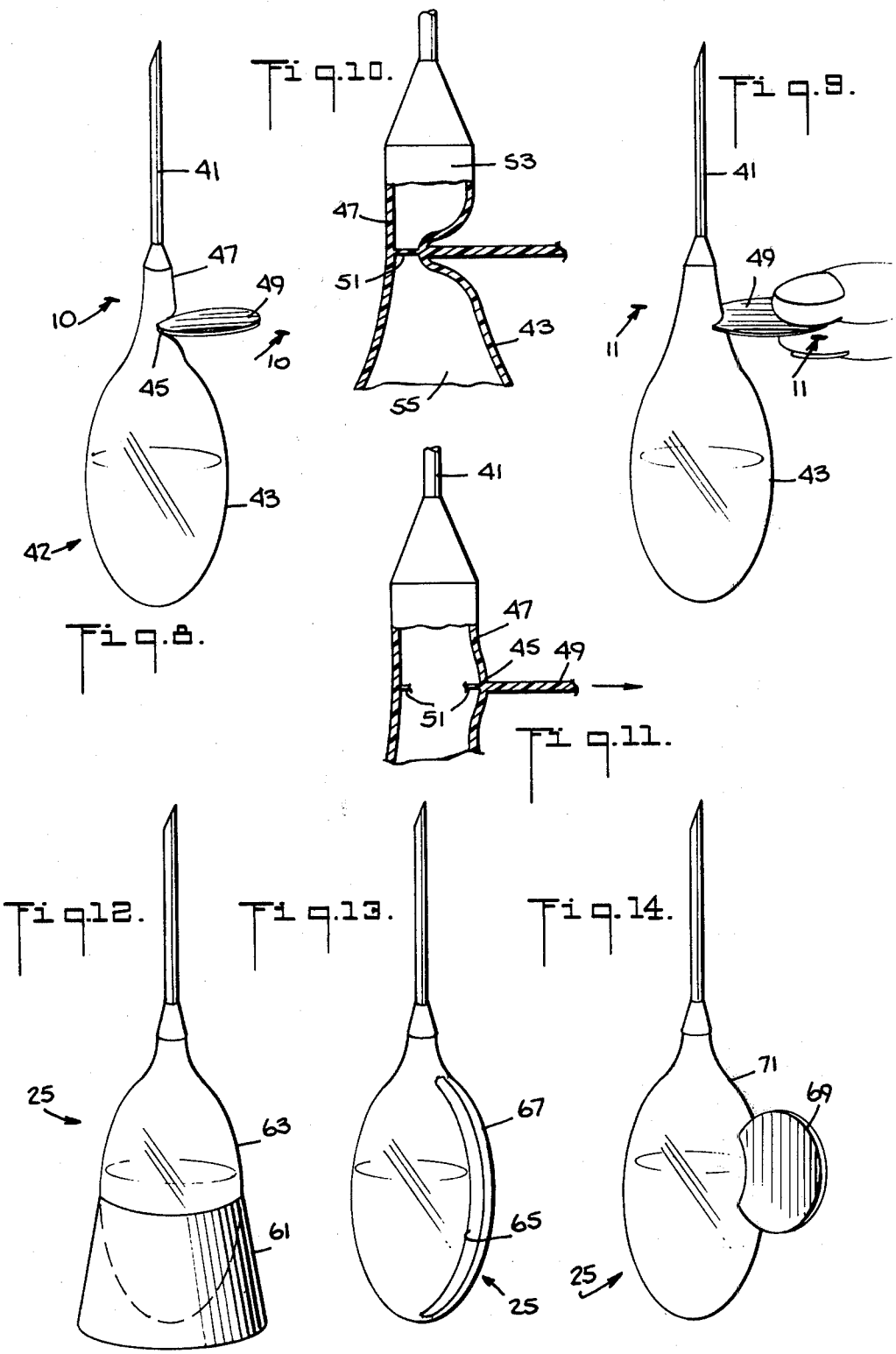

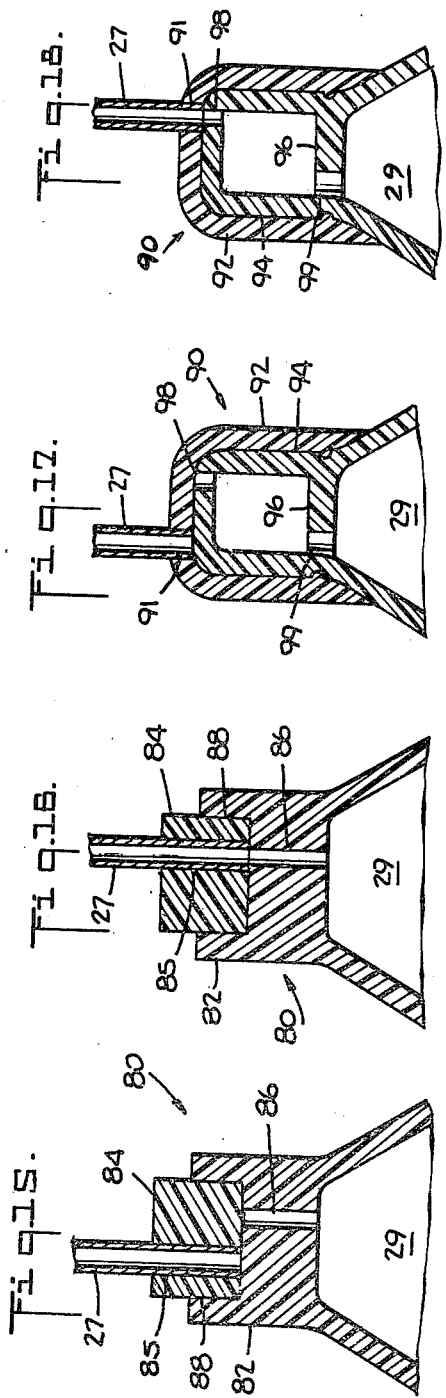

HYPODERMIC SYRINGE

This is a division, of application Ser. No. 501,448, now U.S. Pat. No. 3,989,045, filed Aug. 28, 1974 which was a continuation of application Ser. No. 293,489 filed Sept. 29, 1972 (now abandoned).

BACKGROUND OF THE INVENTION

1. Field of the Invention

This invention relates to a disposable, prefilled hypodermic syringe and to a specially designed ampul adapted for use with a separate hypodermic needle. More particularly, it relates to a hypodermic syringe having a special seal to protect the medicament from bacteria and contamination.

2. Description of the Prior Art

Ampuls for use in conjunction with hypodermic needles have been formed from resin and other plastic material which provides a resiliency or "memory" characteristic whereby the ampul resumes its original shape after compression. See, for example, U.S. Pat. No. 2,615,446 to Lingenfelter. In such prior art, covers for the ampuls are simply mechanically engaged about the neck of the ampul.

In the alternative, U.S. Pat. No. 3,524,445 to Frieze discloses a thin elasic film stretched about and cemented or heat-sealed to the bore of the ampul. Such arrangements are also shown in U.S. Pat. No. 2,757,671 to Haafkens; U.S. Pat. No. 2,388,323 to Henderson; U.S. Pat. No. 2,512,568 to Saffir; U.S. Pat. No. 2,744,527 to Barrett et. al.; and U.S. Pat. No. 3,192,925 to Cunningham. Each of such prior art seals contains an interface between the ampul and the seal which could expose the medicament to the entry of bacteria.

Other patents of general interest include U.S. Pat. Nos. 3,368,557; 3,114,369; 3,090,383; 2,771,879; 2,693,183; and 2,642,064.

The present invention differs in structure and design from the arrangements disclosed in the foregoing patents and provides the following important advantages: (a) no pre-sterilization is needed; (b) no subsequent sterilization is needed; (c) no interface to permit entry of bacteria; and (d) the ampul-syringe unit is readied immediately before introducing the needle into the tissue.

SUMMARY OF THE INVENTION

One embodiment of the present invention relates to a specially designed ampul adapted for use with a separate hypodermic needle to form a hypodermic syringe. The ampul vessel of this embodiment is of a resilient plastic material and has a neck portion which is adapted to engage the hypodermic needle. The ampul has a cap assembly adapted to fit over the neck of the ampul vessel to seal the ampul vessel and maintain the medicament contents in a sterile condition.

In another embodiment of this invention, a prefilled hypodermic syringe consists of a hypodermic needle; an ampul made of a resilient plastic material and a cover assembly positioned over the hypodermic needle and over the mouth of the ampul to maintain the medicament contents of the ampul in a sterile condition.

In both embodiments, the ampul has been formed by use of the technique of plastic blow-molding. Such an ampul is compressible and when the needle has been introduced into the tissue, nothing further has to be pulled, pushed or turned; only finger pressure on the ampul will inject the medicament contents. All air can be expelled from the ampul before introducing the needle into the tissue, thereby taking advantage of the memory characteristics of the wall of the ampul. This allows the position of the needle, whether in or outside of a vein, to be verified. It is an important feature that compression of the ampul with complete expulsion of the air greatly enhances the ease with which, for instance, venous blood can be aspirated. Incomplete removal of the air above the fluid level reduces the force of aspiration. Both embodiments have special seals to maintain sterility of the medicament contents by preventing the entry of bacteria. As a result, no presterilization of either embodiment is needed.

DESCRIPTION OF THE DRAWINGS

FIG. 1 is an isometric view of one embodiment of this invention, an ampul adapted for use with a separate hypodermic needle, and shows both the ampul and the hypodermic needle in their sealed condition.

FIG. 2 is an isometric view of the ampul and hypodermic needle of FIG. 1 showing the seals in the process of being removed from the ampul and from the hypodermic needle.

FIG. 3 is an isometric view of the ampul and hypodermic needle of FIG. 1 and FIG. 2 showing the hypodermic needle affixed to the ampul and ready for use.

FIG. 4 is a vertical, cross-sectional view of part of the ampul of FIG. 1 along the lines 4—4 showing the engagement of the seal to the neck of the ampul.

FIG. 5 is a vertical cross-sectional view of part of an ampul having a threaded neck for engaging a hypodermic needle.

FIG. 6 is a partial vertical cross-section of another embodiment of this invention, a hypodermic syringe consisting of a hypodermic needle, ampul and cover assembly.

FIG. 7 is a partial vertical cross-section of the same embodiment shown in FIG. 6 after the cover assembly has been removed.

FIG. 8 is an isometric view of another embodiment of this invention, a hypodermic syringe consisting of a hypodermic needle and ampul with an appendage in an indentation in the neck of the ampul.

FIG. 9 is an isometric view of the hypodermic syringe shown in FIG. 8 when the appendage is being grasped by the user and pulled to open the membrane in the interior of the ampul.

FIG. 10 is a vertical cross-section of part of FIG. 8 along the lines 10—10.

FIG. 11 is a vertical cross-section of part of FIG. 9 along the lines 11—11.

FIG. 12 is an isometric view of another embodiment of this invention showing an ampul having a circular base portion.

FIG. 13 is an isometric view of another embodiment of this invention showing an ampul having a rigid structural member on the outside of the ampul wall.

FIG. 14 is an isometric view of another embodiment of this invention showing an ampul having a butterfly appendage on the outer wall.

FIGS. 15 and 16 illustrate an alternate embodiment of a closure for an ampul.

FIGS. 17 and 18 illustrate another alternate embodiment of a closure for an ampul.

FIGS. 19 and 20 illustrate another alternate embodiment of a closure for an ampul.

FIGS. 21 and 22 illustrate another alternate embodiment for a closure for an ampul.

FIG. 23 is an isometric view of another embodiment of this invention, an ampul for use with a separate hypodermic needle.

DETAILED DESCRIPTION

Referring to FIG. 1, one embodiment of this invention consists of an ampul, indicated generally by the numeral 1, which is adapted for use with a separate hypodermic needle 3 to form a hypodermic syringe. The ampul 1 consists of an ampul vessel 5 for containing the medicament 7, a neck 9 located at the mouth of the ampul vessel 5, and a cap assembly 11.

The ampul vessel 5 is made of a resilient plastic material formed by the technique of plastic blow-molding and has a hollow interior for containing the medicament contents. The ampul vessel 5 of this embodiment is ovoid and slightly flattened in shape. But, other ampuls of different shape may also be used. The neck portion 9 has an axial bore 4 and is adapted to engage the separate hypodermic needle 3. The cap assembly 11 consists of a cap 13 and one or more tabs 15. The cap 13 is adapted to fit over the neck 9 of the ampul vessel 5 to seal the ampul vessel 5 and maintain the medicament contents of the ampul vessel 5 in a sterile condition by preventing the entry of bacteria. The tabs 15 are permanently affixed to the cap 13 and detachably affixed to the outer surface of the ampul vessel by heat sealing or other bonding process to permit the tab 15 to be grasped by the user and pulled away from the ampul vessel 5 for the purpose of removing the cap 13 from the ampul vessel 5.

FIG. 2 illustrates the same ampul 1 and hypodermic needle 3 as shown in FIG. 1. FIG. 2 shows the hypodermic needle 3 in the process of having its outer seal 17 removed. Similarly, FIG. 2 shows the ampul 1 in the process of having its cap assembly 11 removed so that the hypodermic needle 3 may be fitted over the neck 9 of the ampul vessel 5.

FIG. 3 shows the same ampul 1 and hypodermic needle 3 as shown in FIGS. 1 and 2. In FIG. 3, the hypodermic needle 3 has been affixed to the ampul 1 after the cap assembly 11 has been removed to form a hypodermic syringe ready for use.

FIG. 4 shows the neck 9 of the ampul vessel before the cap assembly 11 has been removed. The neck 9 of the ampul has an axial bore 4 which communicates with the interior of the ampul vessel and a flange 19 which engages the cap 13 of the cap assembly 11. The neck 9 of the ampul has the shape of a truncated cone, indicated as a trapezoid when viewed in cross section as shown in FIG. 4. The top of the cone-shaped neck 9 is located closer to the mouth 21 of the ampul vessel than the base of the cone-shaped neck 9. The base of the cone-shaped neck 9 forms the flange 19 which detachably engages the cap 13 of the cap assembly 11.

Cap 13 is heat-sealed or otherwise bonded to the ampul below the cone-shaped neck 9 of the ampul and along interface 14 in order to insure that bacteria cannot contact the outer surface of the cone-shaped neck. Thus, this surface is maintained sterile prior to the removal of cap assembly 11 and the engagement of the needle therewith. Tension applied to tab 15 by the fingers as shown in FIG. 2 is sufficient to break the seal or bond and enable the cap 13 to be removed immediately before assembly with the needle.

FIG. 3 shows the base 23 of the hypodermic needle being engaged by the neck 9 of the ampul (shown in FIG. 2). The base 23 of the hypodermic needle has the shape of a cone and is dimensioned to fit over the truncated cone formed by the neck 9 of the ampul. The neck 9 has been designed to engage the base 23 of standard disposable hypodermic needle 3 which is a stock item of supply.

FIG. 5 shows an embodiment of the ampul in which neck 9a is provided with threads 24 to engage corresponding threads in base 26 of the cap of the ampul. Neck 9a also includes conically tapered portion 9b which accepts the base 23 of needle 3. The flexibility of the resin material forming the cap assembly enables it to be separated conveniently from the threads.

FIG. 23 illustrates another embodiment of this invention in which ampul 5 is adapted for use with a separate hypodermic needle. Referring to FIG. 23, cap 34 is affixed to ampul 5 by one or more tabs 36. Cap 34 may be a substantially flat disc-shaped cap which is adapted to fit over and cover the bore 38 and the top face of neck 32 of the ampul 5 to maintain the sterility of the ampul contents.

FIGS. 6 and 7 illustrate another embodiment of this invention, a prefilled hypodermic syringe indicated generally by the numeral 25 which consists of a hypodermic needle 27; an ampul 29 for containing the medicament; and a cover assembly, indicated generally by the numeral 31 shown only in FIG. 6. The ampul 29 is made of a resilient plastic material and has a hollow interior for containing the medicament contents. Referring to FIG. 7, the ampul 29 has a neck 33 and a mouth 35. The hypodermic needle 27 which is affixed within the mouth 35 of the ampul 29 engages the interior of the neck 33 and communicates with the interior of the ampul 29.

Referring to FIG. 6, the cover assembly 31 is positioned over the hypodermic needle 27 and over the mouth 35 of the ampul 29. The cover assembly has a plug 37 which fits over the top of the needle 27 and forms a seal bond with respect to the open end of the needle. The cover assembly 31 also has a sleeve 39 extending from the plug 37 over the length of the needle 27 and over the mouth 35 of the ampul 29. The sleeve 39 is detachably heat-sealed or otherwise bonded to the ampul 29 at base 40 to maintain the needle and the neck of the ampul in a sterile condition.

The cross-section of the cover assembly 31 shown in FIG. 6 is the cross-section of a cone in which the plug 37 forms the apex of the cone which is positioned over the needle 27. The line of attachment of the sleeve 39 of the cover assembly 31 forms the base 40 of the cone. The base 40 of the cone-shaped cover assembly 31 is positioned around the ampul 29 and the cover assembly 31 is detachably sealed to the ampul 29 along a line extending around the periphery of the base 40 of the cone where the base 40 rests on the ampul 29.

Thus the sleeve 39 of the cover assembly 31 is sealed to the ampul 29 around the entire periphery of the base 40 of the cone-shaped sleeve 39. This seal maintains the medicament contents of the ampul 29 in a sterile condition by preventing the entry of bacteria into the ampul 29.

Referring again to FIGS. 6 and 7, the ampul 29 of the hypodermic syringe 25 is formed by the technique of plastic blow-molding. The ampul is then filled with a medicament, the hypodermic needle is inserted in the mouth 35 of the ampul 29, and the cover assembly is then heat-sealed or otherwise bonded to the ampul, all done in a continuous process by machine, which excludes the possibility of contamination and eliminates the necessity for preceding or subsequent sterilization. The plastic parts are sterile because of the high temperature of the plastic during the blow-molding procedures. The needle requires pre-sterilization by any of the usual techniques.

Optionally, the cover assembly 31 may have one or more tabs 38 at the base 40 thereof to enable the cover assembly 31 to be more easily pulled away from the ampul 29 in order to break the seal between the base 40 of the cover assembly 31 and the ampul 29 for removing the cover assembly 31 when the hypodermic syringe 25 is ready for use.

FIG. 8 illustrates another embodiment of this invention for a hypodermic syringe 42 having a hypodermic needle 41 and an ampul 43. An indentation 45 is provided in the neck 47 of the ampul 43. An appendage 49 in the form of a tab which is affixed to the indentation 45 on the outside of the neck 47 is adapted to be grasped by the user and pulled (FIG. 9).

Referring to FIG. 10 a membrane 51 is disposed in the interior of the neck 47 of the ampul 43 at the location along the neck 47 where the indentation 45 is located. The indentation is shown in the form of an inwardly directed fold in the wall of neck portion 47. Membrane 51 extends across the neck at the inwardly directed fold. This membrane 51 is sealed around the interior wall of the neck 47 between the mouth 53 of the ampul 43 and the contents 55 inside the ampul 43. The seal of this membrane 51 maintains the medicament contents of the ampul 43 in a sterile condition by preventing the entry of bacteria. When the appendage 49 is grasped and pulled by the user, as shown in FIG. 9, it breaks the membrane 51, as shown in FIG. 11, because the appendage 49 pulls the neck 47 at the point of the indentation 45 exerting a tensional stress on membrane 51 to produce rupture thereof. This rupture of the membrane 51 establishes communication between the ampul 43 and the needle 41.

FIG. 12 illustrates another embodiment of this invention in which a circular base portion 61 is positioned around the bottom of the ampul or ampul vessel 63 to allow the hypodermic syringe 25 to stand upright. The base 61 may be used with the embodiment illustrated in FIGS. 1-5, or the embodiment illustrated in FIGS. 6-7, or the embodiment illustrated in FIGS. 8-11.

FIG. 13 illustrates another embodiment of this invention in which a rigid structural member 65 is provided along a longitudinal axis on the outside of the ampul wall or ampul vessel 67 to give the ampul or ampul vessel 67 stability and to facilitate expulsion of the contents of the ampul. The structural member 65 illustrated in FIG. 13 may be used with the embodiment illustrated in FIGS. 1-5, or the embodiment illustrated in FIGS. 6-7, or the embodiment illustrated in FIGS. 8-11.

FIG. 14 illustrates another embodiment of this invention in which a butterfly-shaped appendage 69 is arranged on the outer wall of the ampul or ampul vessel 71 to facilitate holding the ampul or ampul vessel 71 during injection. The butterfly-shaped appendage 6g may be used with the embodiment illustrated in FIGS. 1-5, or the embodiment illustrated in FIGS. 6-7, or the embodiment illustrated in FIGS. 8-11.

In practice, the ampul or ampul vessel of all of the foregoing embodiments is typically partially filled, for example about half-filled, with medicament and then sealed.

Referring to the alternate embodiment of this invention shown in FIGS. 15 and 16, the sterility of the contents of the ampul 29 is maintained by a specially designed closure 80. The closure 80 includes an ampul cap 82 and a needle base 84. The ampul cap 82 is disposed around the outer circumference of the neck of the ampul and has a longitudinal channel 86 disposed off-center through the ampul cap. The ampul cap 82 also has a well 88 indented in the top of the cap 82.

The needle base 84 is attached to the bottom of the hypodermic needle 27 and has a longitudinal needle channel 85 disposed off-center through needle base 84 in which the hypodermic needle 27 is positioned. The outer circumference of the needle base 84 is dimensioned so that it is smaller than the inner circumference of well 88 of ampul cap 82. As a result, the needle base 84 fits into the well 88 of the ampul cap 82. The fit of needle base 84 into well 88 is a tight fit, but with sufficient tolerance to allow needle base 84 to rotate within well 88. FIG. 15 shows closure 80 in its closed position wherein needle channel 85 is not aligned with cap channel 86 and there is no communication between off-center cap channel 86 and off-center needle channel 85. FIG. 16 shows closure 80 in its open position. Needle base 84 has been rotated to align needle channel 85 with off-center cap channel 86, thereby providing communication between the needle 27 and the interior of ampul 29 through off-center cap channel 86 and off-center needle channel 85.

FIGS. 17 and 18 illustrate another alternate embodiment of a closure 90. The closure 90 for ampul 29 includes an ampul cap 92 and ampul mouth piece 94. Ampul cap 92 has an off-center hole 91 in the top of cap 92. Hypodermic needle 27 is disposed in the hole 91 in cap 92. Cap 92 has an interior circumference which is slightly larger than the exterior circumference of the mouth piece 94. As a result, ampul cap 92 fits over and around ampul mouth piece 94. Ampul mouth piece 94 also has an off-center hole 98 through the top of mouth piece 94 and another off-center hole 99 through a lateral and substantially horizontal appendage 96 disposed in the interior of mouth piece 94. FIG. 17 illustrates closure 90 in its closed position wherein hole 91 and needle 27 of ampul cap 92 are not aligned with off-center hole 98 of mouth piece 94. FIG. 18 illustrates closure 90 in its open position wherein ampul cap 92 to which needle 27 is attached has been rotated so as to align the bottom of needle 27 and hole 91 with off-center hole 98 in the top of ampul mouth piece 94. This established a path of communication from needle 27 through cap hole 91 and through holes 98 and 99 to the interior of ampul 29.

Referring to the alternate embodiment illustrated in FIGS. 19 and 20, the sterility of the contents of the ampul 43 is maintained by a specially designed closure 100. Closure 100 consists of an ampul cap 102 which is attached to needle 41. Needle 41 protrudes through hole 101 in the top of ampul cap 102. The interior diameter at the bottom of ampul cap 102 is slightly larger than the exterior diameter of the neck 47 of ampul 43 so that ampul cap 102 fits around and over the neck 47 of ampul 43. The ampul 43 illustrated in FIGS. 19 and 20 is similar to the ampul 43 illustrated in FIGS. 8, 9, 10 and 11 to the extent that the ampul 43 illustrated in FIGS. 19 and 20 has a membrane 51 in the interior of the neck 47 of ampul 43. This membrane 51 is sealed around interior wall of neck 47 between the mouth of ampul 43 and the contents inside ampul 43. The seal of this membrane 51 maintains medicament contents of ampul 43 in a sterile condition by preventing the entry of bacteria.

Ampul cap 102 has an elongated barb 104 disposed in the interior of ampul cap 102. Before ampul 43 is ready to be used, ampul cap 102 must be depressed from its raised position, as shown in FIG. 19 to its lowered position, as shown in FIG. 20. The depression of ampul cap 102 presses interior barb 104 against membrane 51, thereby rupturing membrane 51 and establishing communications between needle 41 and the interior contents of ampul 43.

Referring to the alternate embodiments illustrated in FIGS. 21 and 22, the sterility of the contents of ampul 43 is maintained by a specially designed closure 110. Closure 110 has a needle base 112. Needle base 112 has a longitudinal channel 116 disposed through the needle base 112 in which needle 41 is placed. The exterior circumference of needle base 112 is slightly smaller than the interior circumference of the neck 47 of ampul 43, whereby the needle base 112 fits within the neck 47 of ampul 43. Needle base 112 also has an elongated barb 118 disposed at the bottom of said needle base 112 within the interior of neck 47 of ampul 43.

The ampul 43 illustrated in FIGS. 21 and 22 is similar to ampul 43 illustrated in FIGS. 8, 9, 10 and 11 to the extent that there is a membrane 51 in the interior of the neck 47 of ampul 43. This membrane 51 is sealed around the interior wall of the neck of ampul 43 between the mouth of the ampul and the contents inside ampul 43. The seal of this membrane 51 maintains the medicament contents of ampul 43 in a sterile condition by preventing the entry of bacteria. When needle base 112 is depressed from its raised condition as shown in FIG. 21 to its lowered condition as shown in FIG. 22, barb 118 presses against and ruptures membrane 51, thereby permitting the interior contents of ampul 43 to communicate with needle 41 through channel 116.

The cover assembly 31 illustrated in FIG. 6 may be used in conjunction with the ampul 43 illustrated in FIGS. 15, 16, 17, 18, 19, 20, 21 and 22.

The ampul of the invention can be formed and filled by machinery operating in a continuous process. In accordance with the process the parison to be blow molded into the ampul is made from either a pre-form or an extruded parison. To simplify the maintaining of the sterility of the parison, the parison can be injection formed or extruded at the blow molding station, that is injection blow-molded. Blow-molding is accomplished by the insertion of a blow pin into what becomes the neck portion of the ampul. Upon withdrawal of the blow pin the formed ampul can be advanced to a filling station at which point a filling nozzle would be inserted into the bore of the ampul. After filling the ampul can be advanced to a sealing station where, by the use of temperature and pressure the ampul can be sealed such as by the sealing of a cap about the neck portion. Of course in the embodiments of the invention in which the needle is mounted in the neck portion of the ampul, the needle would be inserted after filling and before sealing.

The continuous process of injection blow molding the ampul, immediately filling and thereafter immediately closing and sealing the ampul enables the sterility of the interior of the ampul and its contents to be reliably maintained. At the same time the continuous process of blow molding, filling and sealing enables the ampul to be manufactured with desired rates of production.

What is claimed is:

1. A hypodermic syringe comprising a prefilled medicament-containing ampul, a hypodermic needle, said ampul having a wall made of a resilient plastic material defining a medicament-containing chamber, with a hollow neck portion leading to a mouth, said needle affixed to said ampul in communication with said mouth, said wall defining an indentation in said neck portion and decreasing the area across said neck portion thereat, a rupturable membrane disposed across said neck portion at said indentation and providing a fluid seal between said mouth and said chamber to maintain a medicament in said chamber in a sterile condition.

2. The syringe of claim 1 further including means connected to said ampul externally thereof for exerting a rupturing force across said membrane.

3. The syringe of claim 2 wherein said means comprises a tab connected to said wall at said indentation whereby the tab may be pulled substantially in the plane of said membrane to cause rupture thereof.

4. The syringe of claim 1 wherein said indentation is formed by an inwardly directed fold in the wall at said neck portion and said membrane extends across said neck portion at said fold.

5. The syringe of claim 4 further including a tab connected to said wall at said fold whereby said tab may be pulled outwardly with said fold to exert tensional stress on said membrane.

6. A medicament-containing ampul for use in combination with a hypodermic needle, said ampul having a wall made of a resilient plastic material defining a medicament-containing chamber with a hollow neck portion leading to a mouth, said mouth adapted to receive the needle, said wall defining an indentation in said neck portion and decreasing the area across said neck portion thereat, a rupturable membrane disposed across said neck portion at said indentation and providing a fluid seal between said mouth and said chamber to maintain said medicament in a sterile condition.

7. The ampul of claim 6 further including means connected to said wall at said indentation whereby said connected means may be pulled substantially in the plane of said membrane to cause rupture thereof.

8. The ampul of claim 6 wherein said indentation is formed by an inwardly directed fold in the wall at said neck portion and said membrane extends across said neck portion at said fold.

9. The ampul of claim 6 wherein said membrane is formed integrally with said wall and neck portion.

* * * * *